(12) United States Patent
Collins et al.

(10) Patent No.: US 6,719,736 B2
(45) Date of Patent: Apr. 13, 2004

(54) DENTAL SYRINGE WITH DISPOSABLE NEEDLE ASSEMBLY AND REUSABLE PLUNGER ASSEMBLY

(76) Inventors: Margie M. Collins, 4104 Garth Rd., SE., Huntsville, AL (US) 35802; Cary C. Collins, 4104 Garth Rd., SE., Huntsville, AL (US) 35802

( * ) Notice: Subject to any disclaimer, the term of this patent is extended or adjusted under 35 U.S.C. 154(b) by 0 days.

(21) Appl. No.: 10/118,306

(22) Filed: Apr. 6, 2002

(65) Prior Publication Data

US 2002/0147430 A1 Oct. 10, 2002

Related U.S. Application Data

(60) Provisional application No. 60/282,023, filed on Apr. 6, 2001.

(51) Int. Cl.[7] .............................................. A61M 5/00
(52) U.S. Cl. ...................... 604/232; 604/192; 604/110
(58) Field of Search ................................ 604/192, 195, 604/196, 198, 201, 202, 205, 215, 232, 234, 235, 236, 110

(56) References Cited

U.S. PATENT DOCUMENTS

| | | | | |
|---|---|---|---|---|
| 4,553,962 A | * | 11/1985 | Brunet | 604/198 |
| 4,931,040 A | * | 6/1990 | Haber et al. | 604/110 |
| 5,167,641 A | * | 12/1992 | Schmitz | 604/196 |
| 5,201,719 A | * | 4/1993 | Collins et al. | 604/195 |
| 5,279,579 A | * | 1/1994 | D'Amico | 604/192 |
| 5,403,288 A | * | 4/1995 | Stanners | 604/232 |
| 5,514,107 A | * | 5/1996 | Haber et al. | 604/197 |
| 5,522,812 A | * | 6/1996 | Talonn et al. | 604/198 |
| 5,693,023 A | * | 12/1997 | Adams | 604/195 |
| 5,800,403 A | * | 9/1998 | Pressly, Sr. et al. | 604/195 |
| 5,810,775 A | * | 9/1998 | Shaw | 604/110 |
| 5,817,064 A | * | 10/1998 | DeMarco | 604/198 |
| 5,938,641 A | * | 8/1999 | Villanueva | 604/195 |
| 5,989,226 A | * | 11/1999 | Hymanson | 604/198 |
| 6,221,055 B1 | * | 4/2001 | Shaw et al. | 604/232 |

* cited by examiner

Primary Examiner—Sharon Kennedy
(74) Attorney, Agent, or Firm—Curtis W Dodd (57) ABSTRACT

A dental syringe system having a syringe body containing a needle assembly wherein the syringe body serves as a protective shield after medication is injected. A reusable plunger assembly pushes a slidable seal of a carpule and the needle out for medication delivery and then pulls the needle back within the syringe body after the medication is delivered. The needle assembly, syringe body, carpule carrier and carpule are disposable and the plunger is reusable.

34 Claims, 7 Drawing Sheets

DENTAL SYRINGE WITH DISPOSABLE NEEDLE ASSEMBLY AND REUSABLE PLUNGER ASSEMBLY

PRIORITY APPLICATION

This application is related to U.S. Provisional Application Ser. No. 60/282,023 filed on Apr. 6, 2001, entitled "DENTAL SYRINGE WITH DISPOSABLE NEEDLE ASSEMBLY AND REUSABLE PLUNGER ASSEMBLY" and assigned to all the above named inventors, and incorporated by reference herein, with priority claimed for all commonly disclosed subject matter.

BACKGROUND OF THE INVENTION

1. Field of the Invention

The present invention relates to a dental safety syringe having a needle containment safety apparatus and method to protect medical personnel and others from the risk of accidental percutaneous needlestick injuries.

2. Prior Art

Because dental healthcare personnel are at risk of contracting diseases from accidental needle sticks a variety of safety syringes have been developed. Many of the safety syringes have a shield that is placed over the extended needle after medicine has been injected. For example Talonn et al. U.S. Pat. No. 5,522,812 has a shield that is manually placed over the end of an extended needle. Other shields are positioned by sliding a cylindrical shield down the body of the syringe, such as described in Stanners, U.S. Pat. No. 5,403,288. In such designs the hand of the person sliding the shield in place is close to the needle thereby providing some chance of a needle stick.

Another approach for providing a shield of protection from needle sticks is based on moving the extended needle in the proximal direction (retracting the needle) until the needle is contained within the cylindrical body of the syringe. Haber et al. U.S. Pat. No. 4,931,040 modifies the conventional carpule allowing a needle to be retracted and locked within the cylinder of the carpule. Because the Haber invention keeps a person's hand at a greater distance from the extended needle than the above slidable shield devices, the chances of a needle stick are decreased. However the complex modifications to the carpule used by Haber may make the invention too expensive. Another example of retracting the needle within the syringe is described by Sak, U.S. Pat. No. 5,501,670 but requires a special and complex needle retracting unit.

Hence there is a need to provide an improved dental safety syringe for healthcare personnel that provides for safe disposal and has reduced complexity and cost.

SUMMARY OF THE INVENTION

A dental safety syringe that is adapted for use with existing conventional carpules and does not have the complexity of prior art safety syringes has been invented. The novel dental safety syringe of the present invention is easy to operate and an improvement over prior art devices.

In accordance with the present invention a dental syringe for dispensing medication from a carpule with a proximal slidable seal and a distal seal is comprised of a carpule carrier adapted for holding the carpule wherein the carpule carrier has external threads on the proximal end; a syringe assembly having a syringe body containing a slidable needle assembly wherein the syringe assembly has external threads on the proximal end and wherein the syringe assembly is adapted for receiving the carpule carrier, and a plunger assembly adapted for coupling to both of said external threads and having a means for retracting the slidable needle assembly safely inside the syringe body after medication has been dispensed.

A method embodiment of a dental safety syringe for use with a carpule wherein the carpule has a proximal slidable seal and a distal seal comprises the steps of providing a carpule carrier for holding the carpule wherein the carpule carrier has threads on the proximal end, inserting the carpule into the carpule carrier, attaching a plunger assembly to the threads of a syringe assembly, inserting the distal end of the carpule carrier in a syringe assembly wherein the syringe assembly has syringe body and a needle assembly, pushing the needle assembly so that a needle fully extends outside the syringe body and is in a condition for delivering medication, attaching the plunger assembly to the syringe assembly, delivering medication to target tissue; and retracting the needle assembly inside the syringe such that an accidental needle stick is not possible. When the plunger assembly is detached from the combination of the carpule assembly and the syringe assembly, the plunger is available for reuse. The combination of the carpule assembly and syringe assembly, where syringe body securely contains retracted needle, is in condition for disposal.

BRIEF DESCRIPTION OF THE DRAWINGS

The invention can be better understood with reference to the following drawings. The elements of the drawings are not necessarily to scale relative to each other, emphasis instead being placed upon clearly illustrating the principles of the invention. Furthermore, like reference numerals designate corresponding parts throughout several views.

DETAILED DESCRIPTION OF THE INVENTION

Figure 1:
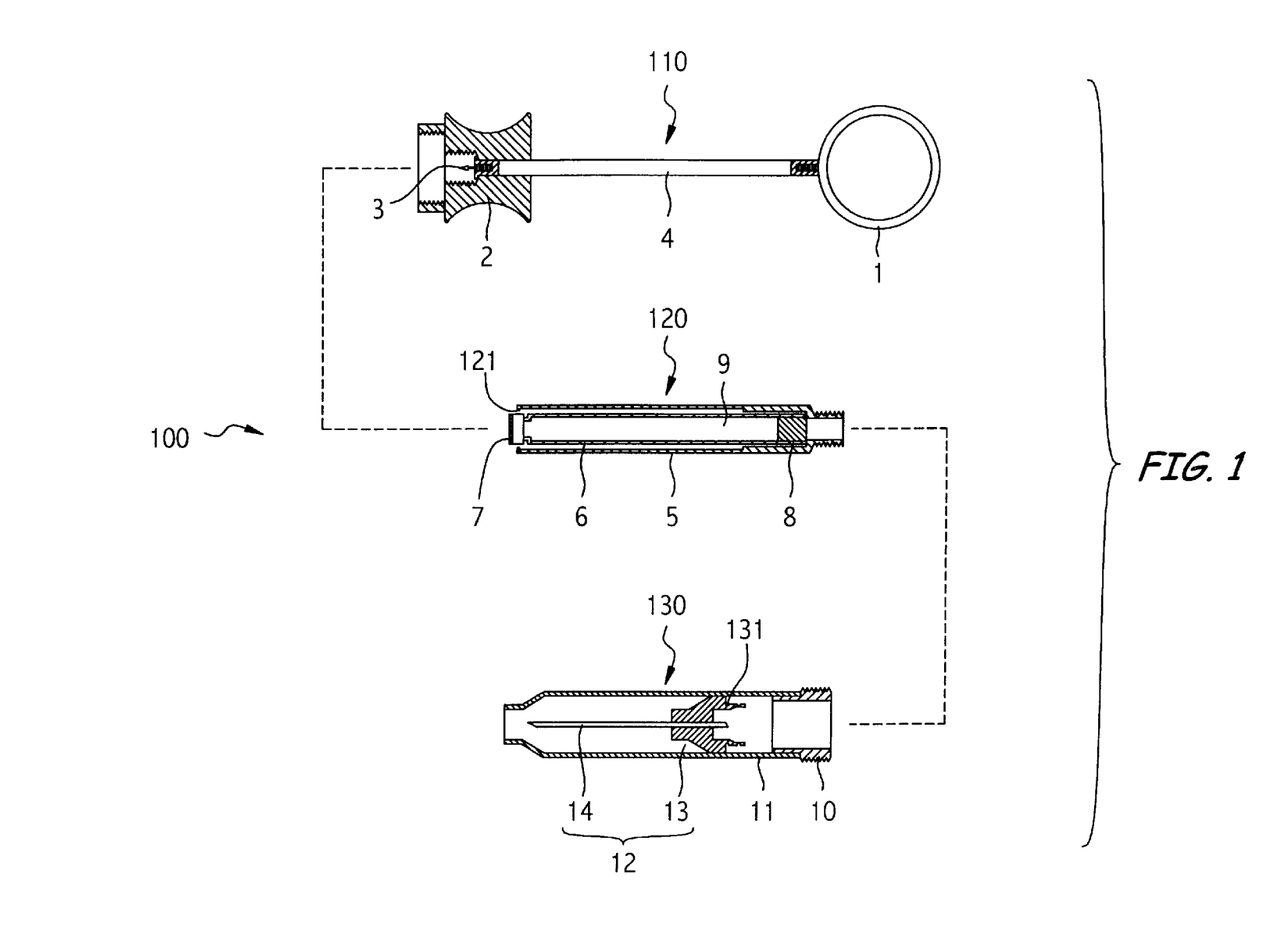
FIG. 1 is illustrates the elements of an embodiment of a dental safety syringe showing the prominent features of each element in accordance with the present invention.

The figures representing a safety syringe are shown as cross sections of components that comprise the present invention. Referring to FIG. 1, a syringe 100 is shown as three elements that will be assembled. The disassembled elements are shown to provide an understanding of the function of the safety dental syringe in accordance with the present invention and describe how the syringe would be used to injected medicine. A plunger assembly 110 is has a plunger shaft 4 with a thumb ring 1 on one end and a harpoon 3 on the other end. The harpoon 3 is attached to the plunger shaft after the shaft has been inserted through a hole in a threaded finger grip 2. The end of the plunger shaft 110 having the thumb ring 1 is called the proximal end of the plunger assembly and the finger grip 2 end of the plunger shaft is called the distal end of the plunger shaft. The terms "proximal" and "distal" have the same meaning when referring to other elements of the safety syringe. Two sets of interior threads are on the inside of the distal end of the plunger assembly 110 and the threads are used to couple a carpule assembly 120 and a syringe assembly 130 as will be seen below.

The carpule assembly 120 has a carpule carrier 5 for holding a carpule 6. The carpule 6 is a cylinder with seals at both ends to contain medication. A distal seal 7 on the distal end of the carpule will allow medicine to exit the carpule when the distal seal is pierced by a needle as will be seen. A slidable proximal seal 8 is initially located on the proximal end of the carpule. When medicine is forced out of the medication compartment 9 the slidable proximal seal is forced towards the distal end of the carpule 6. The carpule 6 is a conventional or standard container for holding and dispensing medicine. As shown there is an opening at the distal end of the threaded carpule carrier for receiving the carpule. A wedge shaped ridge 121 that extends inwardly is located on the distal end of the carpule carrier. The ridge serves one element of a latch for coupling the carpule carrier to a groove in a needle carrier 13.

A third part of the safety syringe is a syringe assembly 130. The syringe assembly 130 has a threaded internal stop 10 inserted in the proximal end of a syringe body 11. The threads of the internal stop will be coupled to one of the thread sets on the finger grip 2. The distal end of the threaded internal stop, that is inserted inside the syringe body 11, provide a stop for keeping a needle hub 13 from leaving the syringe body as will be seen in the discussion of FIG. 7. The needle hub 13 has a needle 14 with a lumen going through the center of the hub and the needle is securely attached to the needle hub. The combination of the needle hub 13 and needle 14 are referred to as a needle assembly 12. It should be noted that there is a notch 131 facing outward on the proximal end of the needle hub 13 and the notch serves as a second part of a snap latch that attaches the carpule carrier 120 to the needle hub.

FIGS. 2–8 illustrate steps for assembly and disassembly of the safety syringe of the present invention. It is helpful to note before discussing the steps that both the carpule assembly 120 and syringe assembly 130 are disposable, but that the plunger assembly 110 is reusable.

Figure 2:
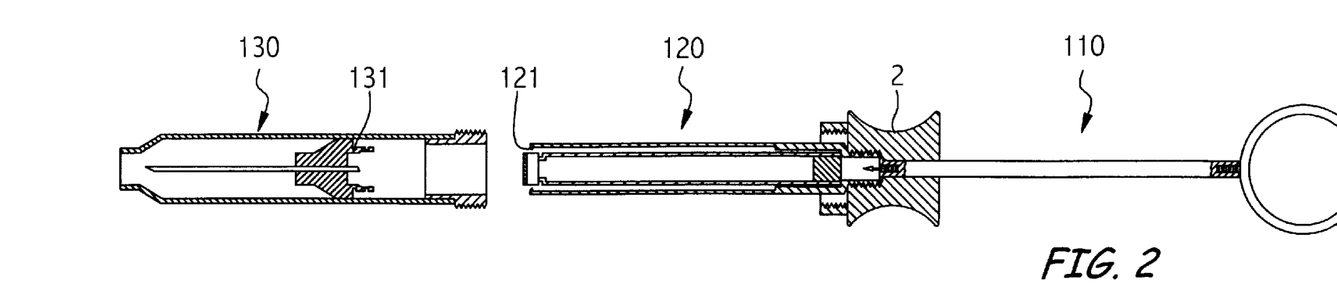
FIG. 2 illustrates a first step in assembling the components of FIG. 1.

A first step (or operation 1) for the assembly of the safety syringe 100 is to attach the plunger assembly 110 to the carpule assembly 120. FIG. 2 illustrates external (on the outside and at the proximal end) threads of the threaded carpule carrier 5 secured to the first set of interior threads of the threaded finger grip 2 where the first set of threads is the set having the smallest diameter. The first step is attaching carpule assembly 120 to the plunger assembly 110 by placing the proximal end of the carpule assembly inside the distal end of the plunger assembly 110 and screwing the units together until the carpule assembly and plunger assembly are firmly attached. Note that there is a space between the second set of threads (interior threads) of the threaded finger grip 2 and the outside of the proximal end of the carpule assembly 120.

Figure 3:
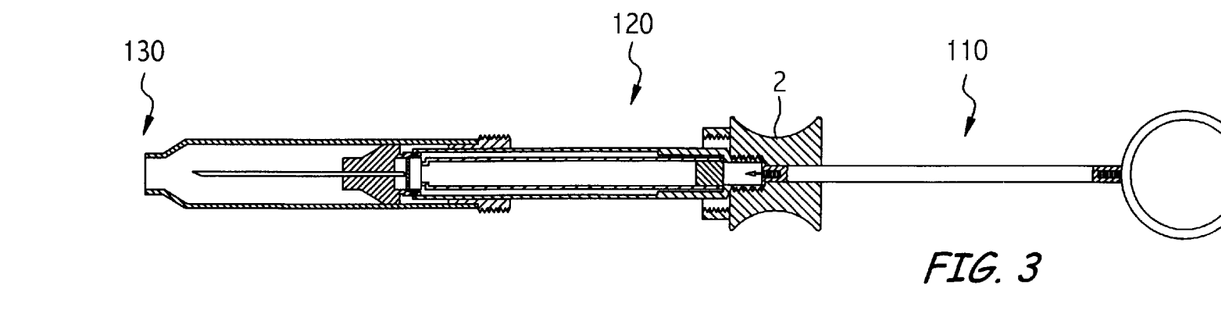
FIG. 3 illustrates a second step in assembling the components of FIG. 1.
Figure 4:
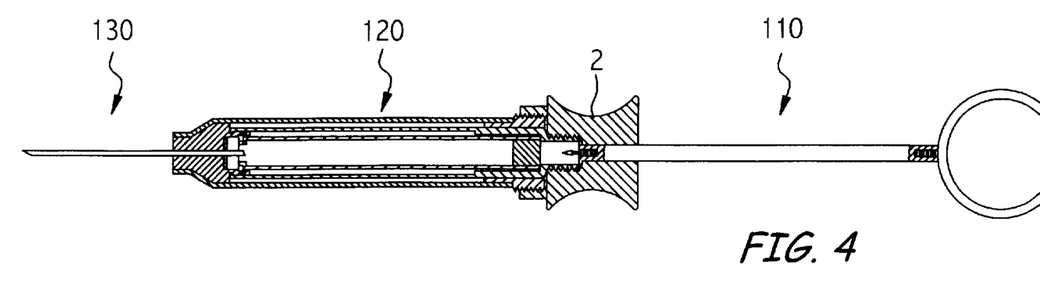
FIG. 4 illustrates a third step in assembling the components of FIG. 1.

Referring now to FIG. 3 for a second step of assembly. The combination of the plunger assembly 110 and carpule carrier 120 is inserted in an opening on the proximal end of the syringe assembly 130. The combination is pushed in the distal direction until the needle is completely extruded out of a tapered opening at the distal end of the syringe body 11 and the tapered end of the needle assembly 12 fits within the tapered opening of the syringe body. Next, step 3, the syringe assembly is securely attached to the second set of threads on the plunger assembly 110. After step 3 is completed both the syringe assembly 130 and the carpule assembly 120 are securely attached to the plunger assembly 110 as illustrated in FIG. 4. Also during step 3 the proximal end of the needle 14 pierces the distal seal 7 of the carpule 6 so that medication may be delivered through the lumen of the needle. In addition when step 3 is completed the wedge shaped ridge 121 snaps into the groove 131 of the needle hub 13 thereby locking the distal end of the threaded carpule carrier 5 to the proximal end of needle assembly 12.

Figure 5:
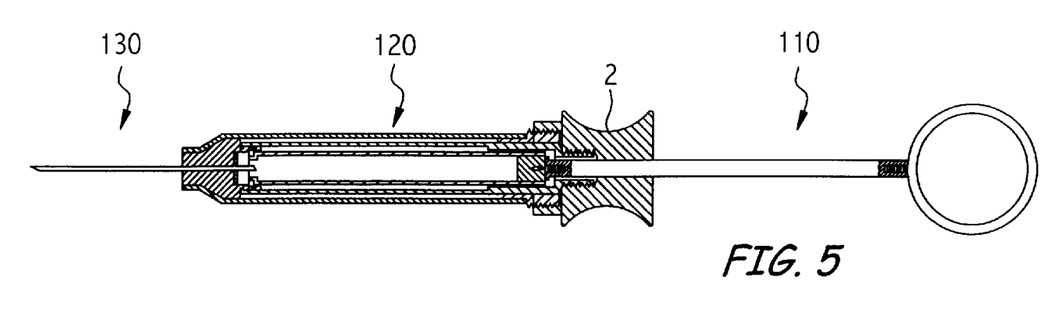
FIG. 5 illustrates a fourth step in assembling the components of FIG. 1.
Figure 6:
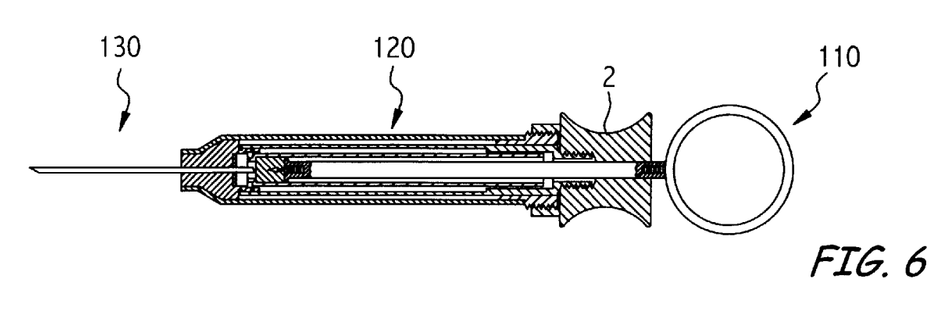
FIG. 6 illustrates a fifth step in assembling the components of FIG. 1.

Step 4, illustrated in FIG. 5, is the step of pushing the harpoon 3 of the plunger assembly 110 into the proximal slidable seal 8 of the carpule. After the harpoon 3 is attached to the proximal slidable seal 8, medicine is injected into target tissue by pushing the plunger shaft 4 in the distal direction using the thumb ring 1 and threaded finger grip 2, step 5. After the medicine is injected the disassembly steps begin.

Figure 7:
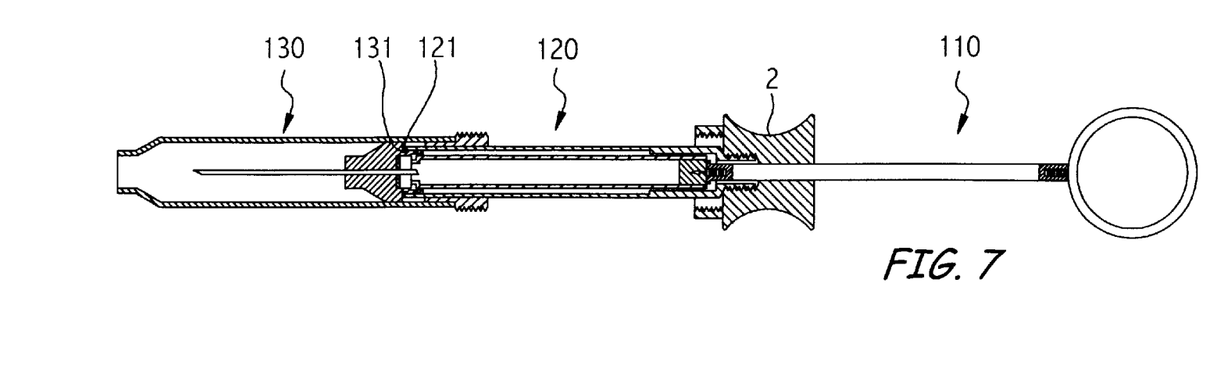
FIG. 7. illustrates a sixth step in assembling the components of FIG. 1.
Figure 8:
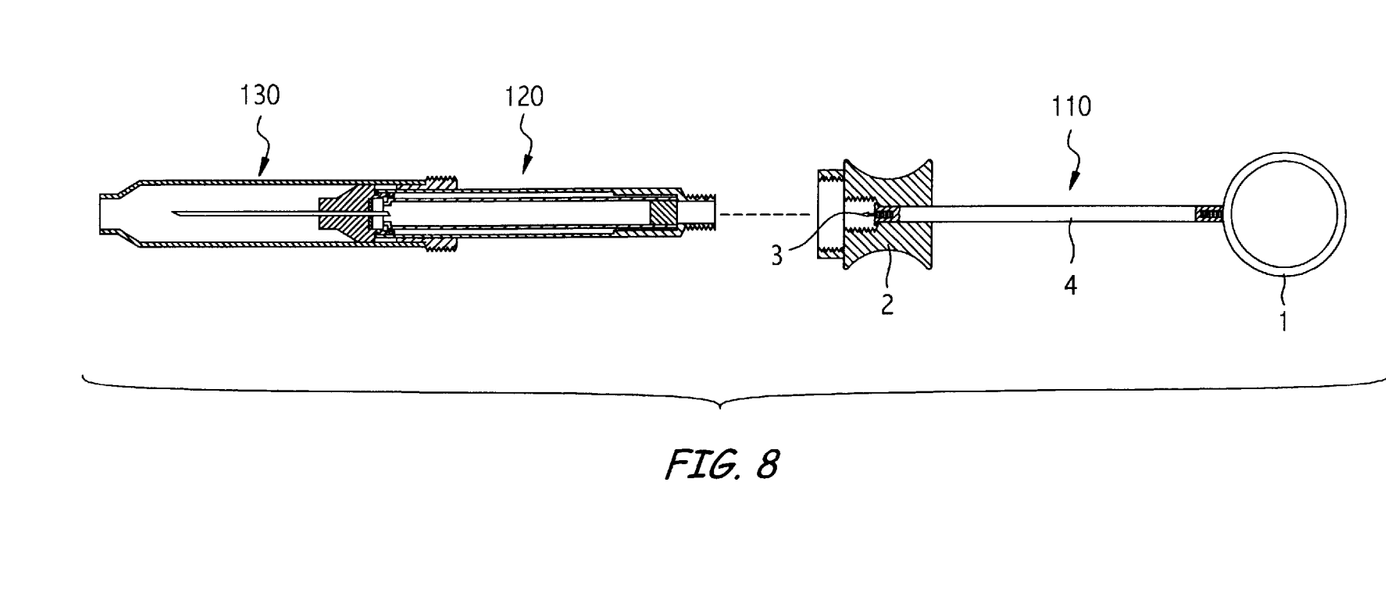
FIG. 8. illustrates a seventh step in assembling the components of FIG. 1.

As illustrated in step 6 of FIG. 7, the carpule assembly 120 is pulled, using the plunger assembly, in the proximal direction until the needle hub reaches the stop within the syringe assembly 130. It should be noted that the needle assembly and carpule assembly are locked together with the wedge shaped ridge 121 and the groove 131. As shown in FIG. 7, it is necessary to separate the syringe assembly 130 from the plunger assembly 110 by unscrewing the threaded finger grip 2 from the syringe assembly 130 before pulling the carpule assembly 120 in the proximal direction and towards the proximal end of the syringe body 11. When step 6 is complete the needle 14 is completely inside the syringe body 11 and the syringe body now serves as a shield for protection from a needle stick. The final step of disassembly, step 7, is detaching by unscrewing the plunger assembly 110 from the threads on the proximal end of the carpule assembly 120. After step 7 is complete the syringe assembly 130 and the carpule assembly 120 are coupled together forming a disposable unit. Because force is required to move the needle assembly the needle is secured in the retracted position. The plunger assembly 110 is now available for reuse.

Figure 9:
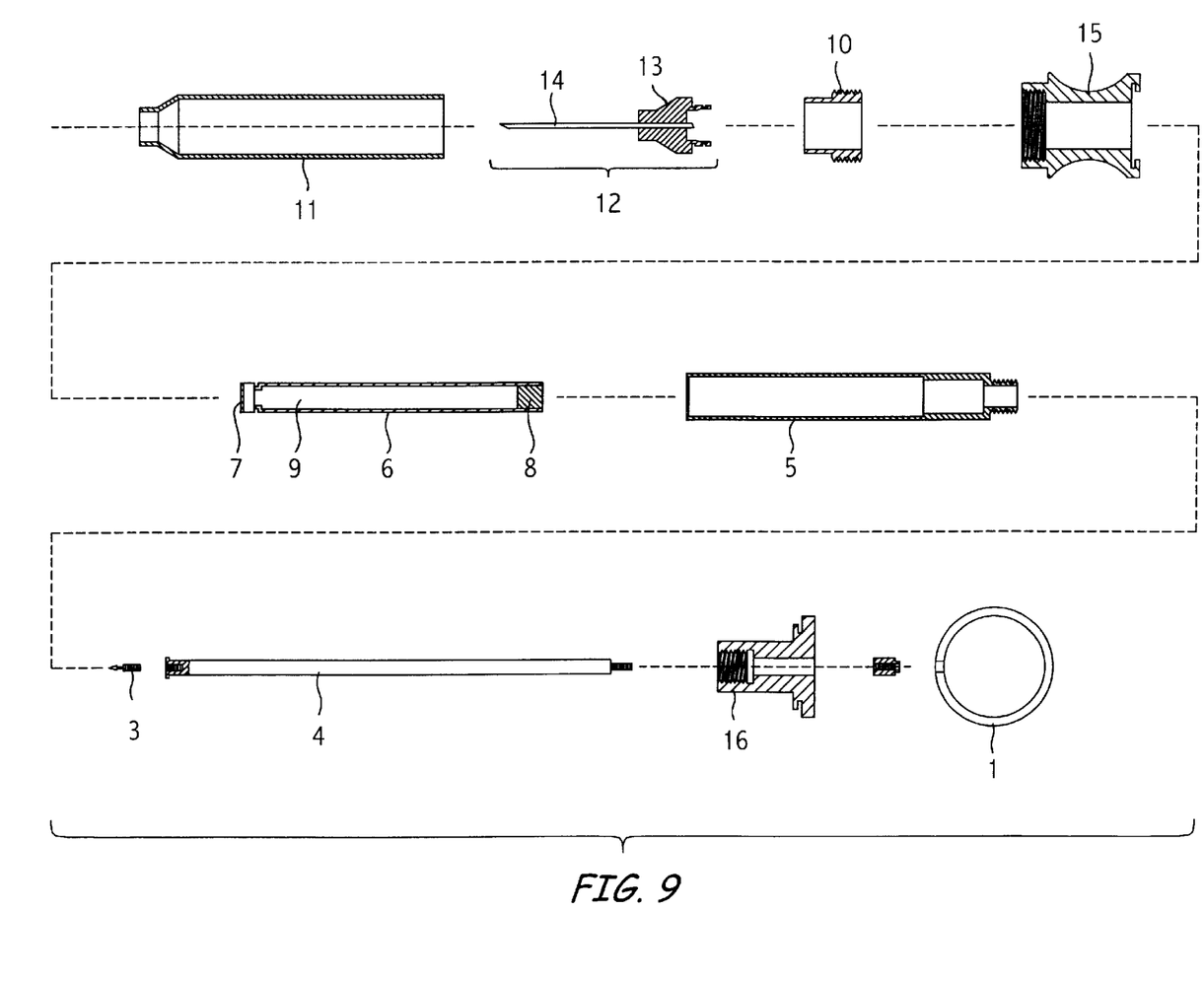
FIG. 9. is a drawing of elements of a second embodiment of a dental syringe in accordance with the present invention.

A second embodiment of the present invention is illustrated in FIG. 9 with the assembly and disassembly steps shown in FIGS. 10–17. For the second embodiment a modified finger grip 15 becomes part of the syringe assembly 130 and the threaded sleeve 16 replaces the finger grip 2 of the first embodiment. The syringe body 11 still serves as a shield as in the first embodiment and the ridge 121 and groove 131 are used to lock the carpule assembly 120 to the needle hub 13.

FIG. 9 illustrates the three elements of the second embodiment of the dental safety syringe of the present invention. The carpule assembly of FIG. 9 has the threaded carpule carrier 5 and the carpule 6 as previously illustrated in FIG. 1. A modified syringe assembly 130 has the syringe body 11, the needle assembly 12, the threaded internal stop 10 but now has a threaded finger grip 15. The plunger assembly 110 has the plunger shaft 4 with the harpoon 3, the thumb ring 1 but now has a threaded sleeve 16. The arrangement for assembly of the three elements 110, 120, and 130 is illustrated in FIG. 10.

Figures 10, 11:
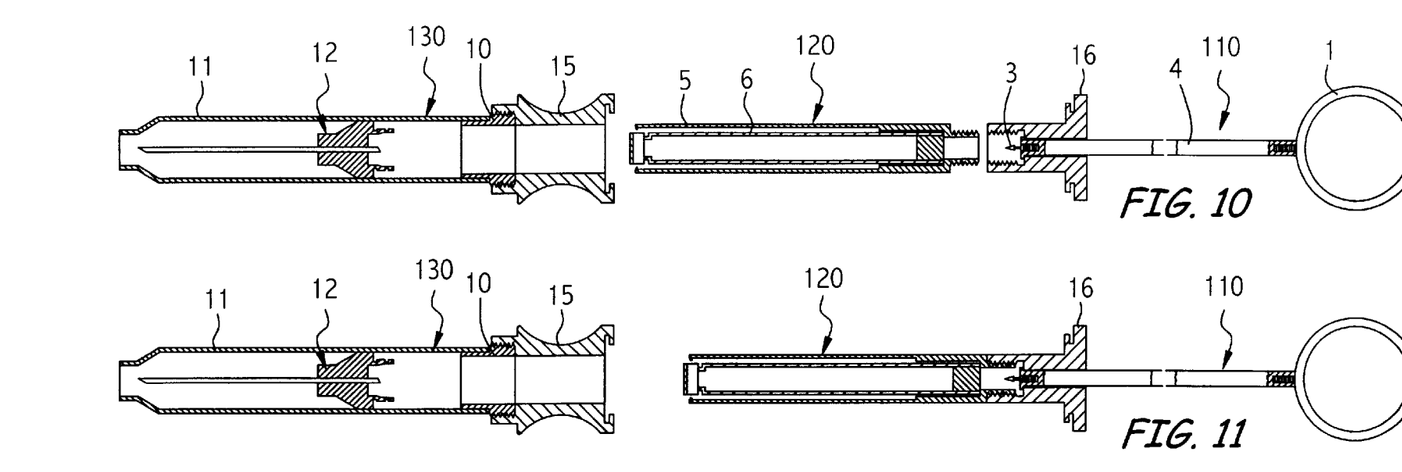
FIG. 10 illustrates the elements of FIG. 9 partially assembled.
FIG. 11 illustrates a first step in assembling the components of FIG. 10.
Figure 12:
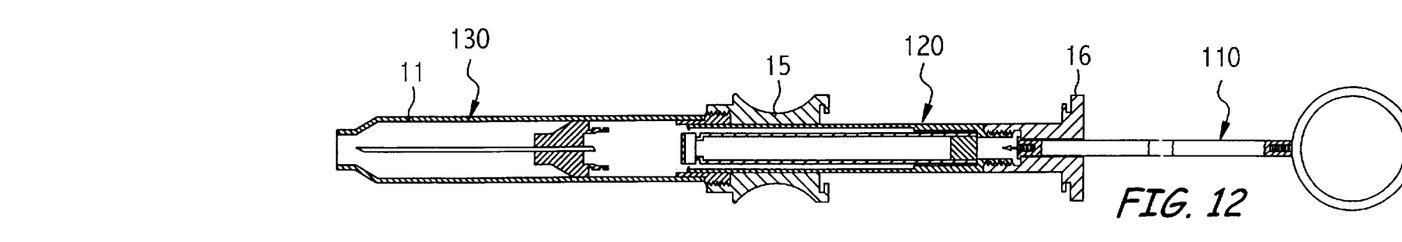
FIG. 12 illustrates a second step in assembling the components of FIG. 10.
Figure 13:
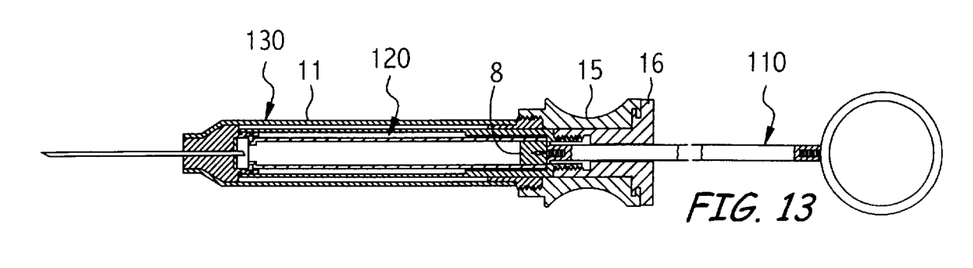
FIG. 13 illustrates a third step in assembling the components of FIG. 10.
Figure 14:
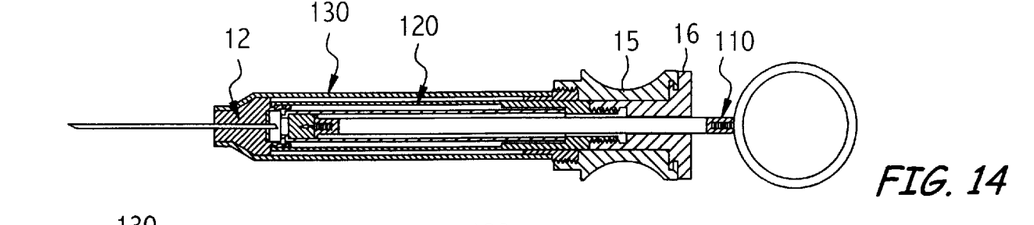
FIG. 14 illustrates a fourth step in assembling the components of FIG. 10.

FIGS. 10–17 illustrate steps for assembling and disassembling of the second embodiment of the present invention. FIG. 10 illustrates an alignment of the elements before assembly. First the carpule assembly 120 is attached to the plunger assembly 110 by screwing the units together, step 1 as illustrated in FIG. 11. Next, step 2 the distal end of the carpule assembly 120 is inserted into the proximal end of the syringe assembly 130 as shown in FIG. 12. After the carpule assembly 120 and needle assembly 12 are pushed forward, the threaded sleeve 16 is securely reversibly coupled the threaded finger grip 15 by locking tabs on the threaded sleeve 16 to a groove in the threaded finger grip, step 3. A bayonet type coupling for step 3 would be understood by those skilled in the art. During step 3 the harpoon 3 is pierces and is attached to the proximal slidable seal 8 of the carpule 6 and the proximal end of the needle penetrates the distal seal making medication available for delivery. After medication is injected into target tissue, step 4 shown in FIG. 14 the disassembly steps begin.

Figures 15, 16:
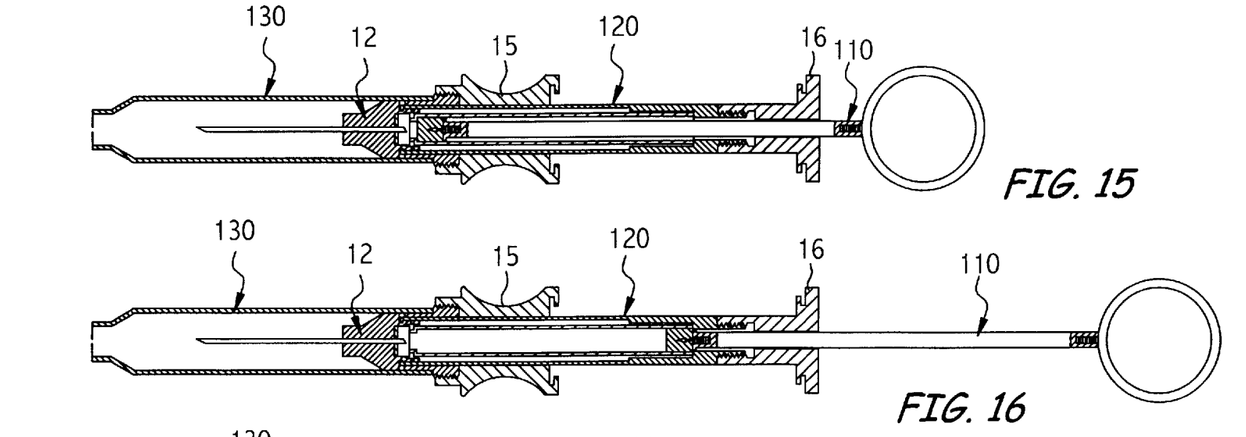
FIG. 15 illustrates a fifth step in assembling the components of FIG. 10.
FIG. 16. illustrates a sixth step in assembling the components of FIG. 10.
Figure 17:
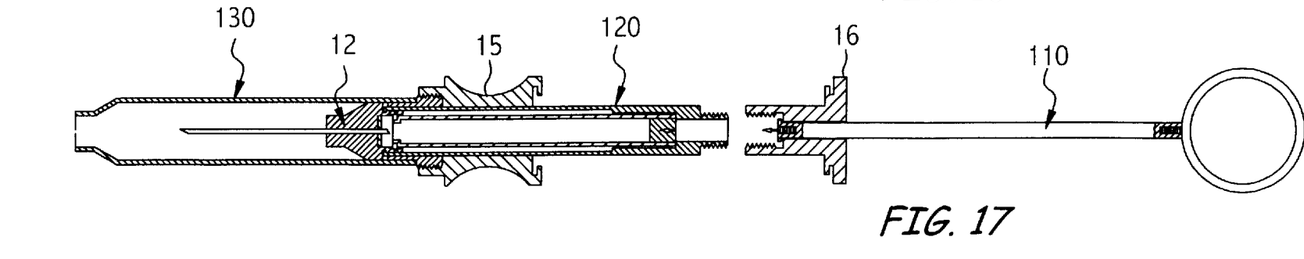
FIG. 17. illustrates a seventh step in assembling the components of FIG. 10.

To disassemble the threaded sleeve 16 with the bayonet type coupling is detached from the threaded finger grip 15 and the carpule assembly is pulled in the proximal direction, step 5 as shown in FIG. 15. Next the proximal slidable seal is pulled in the proximal direction until the needle hub 13 reaches the stop in the syringe assembly 130 as shown in FIG. 16, step 6. When the threaded sleeve is unscrewed from the external threads on the proximal end of the carpule assembly 120, the plunger assembly 110 is separated from the combination of the carpule assembly 120 and the syringe assembly 130. The above combination is disposable. The plunger assembly 110 is now ready for re-use. As in the first embodiment the syringe body serves as a shield from the needle. In addition the disposable elements for both embodiments are the syringe assembly 130 and the carpule assembly 120.

All such modifications and variations of the embodiments of the dental safety syringe are intended to be included herein and are within the scope of this disclosure that is protected by the following claims.

We claim:

1. A syringe for dispensing medication comprising:
   a carpule assembly containing medication, the carpule assembly having a proximal slidable seal and a distal seal;
   a syringe assembly comprising a syringe body containing a slidable needle assembly wherein the syringe body is adapted for proximally receiving the carpule assembly and wherein the carpule assembly locks to the needle assembly; and
   a plunger assembly adapted to reversibly couple to the syringe assembly and to reversibly couple to the carpule assembly and wherein the plunger assembly extends the needle, and delivers medication when pushed in the distal direction and retracts the needle assembly within the syringe body when moved in the proximal direction after medication is delivered.

2. The syringe of claim 1 wherein the plunger assembly further comprises a plunger shaft with a harpoon wherein the harpoon reversibly secures the plunger shaft to the proximal seal.

3. The syringe of claim 2 wherein the plunger assembly is reusable.

4. The syringe of claim 1 wherein the needle assembly comprises a needle hub and a needle.

5. The syringe of claim 4 wherein the proximal end of the needle hub has a groove for coupling to a wedge-shaped ridge on the carpule assembly.

6. The syringe of claim 2 wherein the plunger assembly has a thumb ring and a finger grip.

7. A method for providing a syringe for delivering medication the method having the steps of:
   providing a carpule assembly for holding medication, the carpule assembly having a slidable seal and a stationary seal;
   inserting the carpule assembly into a syringe assembly containing a needle assembly and irreversibly attaching the carpule assembly to the needle syringe needle;
   reversibly coupling a plunger assembly to the carpule assembly and the syringe assembly;
   pushing the needle assembly in the distal direction with the plunger assembly so that a needle is fully extended outside the syringe body and delivers medication to a target tissue when the plunger assembly moves the slidable seal in the distal direction; and
   retracting the needle assembly inside the syringe body such that the needle is unable to cause needle stick.

8. The method of claim 7 having the additional step of detaching the plunger assembly from the syringe assembly.

9. The method of claim 8 having the further step of disposing of the carpule assembly, the carpule and the syringe assembly.

10. A syringe for dispensing medication comprising:
    a carpule assembly for containing the medication and having a proximal slidable seal and a distal seal, the carpule assembly adapted to reversibly couple to a plunger assembly; and
    a syringe assembly comprising a syringe body and a slidable needle assembly wherein the syringe assembly is adapted for receiving and locking to the carpule assembly and for delivering the medication upon the urging of a plunger shaft of the plunger assembly that is reversibly coupled to the syringe assembly and reversibly coupled to the carpule assembly, and wherein the syringe body serves as a protective shield when the needle assembly is pulled in the proximal direction after medication delivery is complete.

11. The syringe of claim 10 wherein the coupling between the carpule assembly and the plunger assembly is a threaded coupling.

12. The syringe of claim 10 wherein the coupling between the plunger assembly and the syringe assembly is a bayonet coupling.

13. The syringe of claim 12 wherein plunger assembly is reusable.

14. The syringe of claim 10 wherein the carpule assembly and syringe assembly are disposable.

15. The syringe of claim 10 wherein the carpule assembly has a ridge adapted to couple to a groove in the hub of the needle assembly.

16. The syringe of claim 10 wherein the carpule assembly and syringe assembly are adapted to extract medication.

17. A syringe for dispensing medication comprising:
a syringe assembly comprising a syringe body containing a slidable needle assembly having a needle secured within a slidable hub; and
a plunger assembly having reversibly coupled to a carpule assembly with a slidable seal coupled to a plunger shaft and a stationary distal seal for receiving the proximal end of the needle, the carpule assembly further having a ridge on the distal end of the carpule assembly for coupling to a groove in the slidable hub, the plunger assembly adapted for reversibly coupling to the syringe assembly wherein the plunger assembly is coupled to the syringe assembly for delivering medication and is uncoupled when delivery of medication is complete and the needle is pulled in the proximal direction and retracted within the syringe body.

18. The syringe of claim 17 wherein the coupling is a threaded coupling.

19. The syringe of claim 17 wherein the coupling is a bayonet coupling.

20. The syringe of claim 17 wherein the needle assembly is secured within the syringe body.

21. A dental syringe for dispensing medication from a carpule having a proximal slidable seal and a distal seal, the dental syringe comprising:
a carpule carrier adapted for holding the carpule wherein the carpule carrier has external threads on the proximal end;
a syringe assembly comprising a syringe body containing a slidable needle assembly wherein the syringe assembly has external threads on the proximal end and wherein the syringe assembly is adapted for receiving the carpule carrier;
a plunger assembly having two sets of internal threads adapted for coupling to said external threads, the plunger assembly coupled to the slidable needle assembly for extending the needle for medication delivery and retracting the needle assembly within the syringe body after medication has been delivered.

22. The dental syringe of claim 21 wherein the plunger assembly further comprises a plunger shaft with a harpoon wherein the harpoon reversibly secures the plunger shaft to the proximal seal.

23. The dental syringe of claim 22 wherein the plunger assembly is reusable.

24. The dental syringe of claim 21 wherein the needle assembly comprises a needle hub and a needle.

25. The dental syringe of claim 24 wherein the proximal end of the needle hub has a groove for coupling to an internal ridge on the carpule carrier.

26. The dental syringe of claim 22 wherein the plunger assembly has a thumb ring and a finger grip.

27. A method for providing a dental safety syringe for use with a carpule wherein the carpule has a proximal slidable seal and a distal seal comprising the method having the steps of:
providing a carpule carrier for holding the carpule wherein the carpule carrier has threads on the proximal end of the carpule carrier;
inserting the carpule into the carpule carrier;
attaching a plunger assembly to the threads of a syringe assemby;
inserting the distal end of the carpule carrier in a syringe assembly wherein the syringe assembly has syringe body and a needle assembly;
pushing the needle assembly in the distal direction with the plunger assembly so that a needle is fully extended outside the syringe body and in a condition for delivering medication;
attaching the plunger assembly to the syringe assembly;
delivering medication to target tissue; and
retracting the fully extended needle inside the syringe body such that the needle is unable to cause needle stick.

28. The method of claim 27 having the additional step of detaching the plunger assembly from the syringe assembly.

29. The method of claim 28 having the further step of disposing of the carpule assembly, the carpule and the syringe assembly.

30. A dental syringe for dispensing medication from a carpule having a proximal slidable seal and a distal seal, the dental syringe comprising:
a carpule carrier adapted for holding the carpule wherein the carpule carrier has external threads on the proximal end;
a syringe assembly comprising a syringe body containing a slidable needle assembly wherein the syringe assembly has external threads on the proximal end and wherein the syringe assembly is adapted for receiving the carpule carrier;
a plunger assembly having two sets of internal threads adapted for coupling to said external threads, the plunger assembly coupled to the slidable needle assembly for extending the needle for medication delivery and retracting the needle assembly within the syringe body after medication has been delivered.

31. The dental syringe of claim 30 wherein the reversible coupling is a bayonet type coupling.

32. The dental syringe of claim 30 wherein the plunger assembly is detached from the syringe assembly after the needle is retracted.

33. The dental syringe of claim 32 wherein the finger grip is reusable.

34. The dental syringe of claim 12 wherein the needle is securely contained within the syringe assembly.

* * * * *